(12) United States Patent
Wilson et al.

(10) Patent No.: US 6,428,988 B1
(45) Date of Patent: *Aug. 6, 2002

(54) METHODS USING CRE-LOX FOR PRODUCTION OF RECOMBINANT ADENO-ASSOCIATED VIRUSES

(75) Inventors: James M. Wilson, Gladwyne; Daniel Phaneuf, Philadelphia, both of PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/923,726

(22) Filed: Aug. 7, 2001

Related U.S. Application Data

(63) Continuation of application No. 09/242,743, filed as application No. PCT/US97/15691 on Sep. 4, 1997, now Pat. No. 6,274,354.
(60) Provisional application No. 60/025,323, filed on Sep. 6, 1996, now abandoned.

(51) Int. Cl.[7] .......................... C12N 15/63; C12N 15/64
(52) U.S. Cl. ............................. 435/91.41; 435/320.1; 435/91.4; 435/91.42; 435/456; 435/462; 435/325; 435/366; 435/369; 435/457
(58) Field of Search .......................... 435/235.1, 320.1, 435/91.4, 91.41, 91.42, 456, 462, 325, 366, 369, 457, 455

(56) References Cited

U.S. PATENT DOCUMENTS 5,139,941 A  8/1992  Muzyczka

FOREIGN PATENT DOCUMENTS

| WO | WO95/13365 A1 | 5/1995 |
| WO | WO95/13392 A1 | 5/1995 |
| WO | WO96/17947 A1 | 6/1996 |
| WO | WO97/06272 A1 | 2/1997 |

OTHER PUBLICATIONS

M. Anton et al, "Site–Specific Recombination Mediated by an Adenovirus Vector Expressing the Cre Recombinase Protein: a Molecular Switch for Control of Gene Expression", J. Virol., 69(8):4600–4606 (Aug., 1995).

A. Beaton et al, "Expression from the Adeno–Associated Virus p5 and p19 Promotors is Negatively Regulated in trans by the rep Protein", J. Virol., 63(10):4450–4454 (Oct., 1989).

B. Carter, "The Growth Cycle of Adeno–Associated Virus", in CRC Handbook of Parvoviruses, vol. 1, Chapter 10, pp. 155–168, ed. P. Tijssen, CRC Press, Inc., Boca Raton, Florida (1990).

T. Flotte et al, "Stable in vivo Expression of the Cystic Fibrosis Transmembrane Conductance Regulator with an Adeno–Associated Virus Vector", Proc. Natl. Acad. Sci. USA, 90:10613–10617 (Nov., 1993).

Y. Kanegae et al, "Efficient Gene Activation System on Mammalian Cell Chromosomes Using Recombinant Adenovirus Producing Cre Recombinase", Gene, 181(1–2):207–212 (Nov., 1996).

Y. Kanegae et al, "Efficient Gene Activation in Mammalian Cells by Using Recombinant Adenovirus Expressing Site–Specific Cre Recombinase", Nucleic Acids Research, 23(19):3816–3821 (Oct., 1995).

N. Kilby et al, "Site–Specific Recombinases: Tools for Genome Engineering", Trends Genet., 9(12):413–421 (Dec., 1993).

R. Kotin, "Prospects for the Use of Adeno–Associated Virus as a Vector for Human Gene Therapy", Human Gene Therapy, 5:793–801 (Jul., 1994).

J. Li et al, "Role for Highly Regulated rep Gene Expression in Adeno–Associated Virus Vector Production", J. Virol., 71(7):5236–5243 (Jul., 1997).

M. Snaith et al, "Multiple Cloning Sites Carrying loxP and FRT Recognition Sites for the Cre and Flp Site–Specific Recombinases", Gene, 166(1):173–174 (Jan., 1995).

P. Wang et al, "High Frequency Recombination Between loxP Sites in Human Chromosomes Mediated by an Adenovirus Vector Expressing Cre Recombinase", Somatic Cell and Molecular Genetics, 21(6):429–441 (Nov., 1995).

*Primary Examiner*—David Guzo
*Assistant Examiner*—Maria Marvich
(74) *Attorney, Agent, or Firm*—Howson and Howson

(57) ABSTRACT

Methods for efficient production of recombinant AAV are described. In one aspect, three vectors are introduced into a host cell. A first vector directs expression of cre recombinase, a second vector contains a promoter, a spacer sequence flanked by loxP sites and rep/cap, and a third vector contains a minigene containing a transgene and regulatory sequences flanked by AAV ITRs. In another aspect, the host cell stably or unducibly expresses cre recombinase and two vectors carrying the other elements of the system are introduced into the host cell.

6 Claims, 8 Drawing Sheets

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
       (A) LENGTH: 10398 base pairs
       (B) TYPE: nucleic acid
       (C) STRANDEDNESS: double
       (D) TOPOLOGY: unknown (ii) MOLECULE TYPE: cDNA (xi) SEQUENCE DESCRIPTION: SEQ ID NO: 1:

```
GAATTCGCTA GCATCATCAA TAATATACCT TATTTTGGAT TGAAGCCAAT ATGATAATGA     60
GGGGGTGGAG TTTGTGACGT GGCGCGGGGC GTGGGAACGG GGCGGGTGAC GTAGTAGTGT    120
GGCGGAAGTG TGATGTTGCA AGTGTGGCGG AACACATGTA AGCGACGGAT GTGGCAAAAG    180
TGACGTTTTT GGTGTGCGCC GGTGTACACA GGAAGTGACA ATTTTCGCGC GGTTTTAGGC    240
GGATGTTGTA GTAAATTTGG GCGTAACCGA GTAAGATTTG GCCATTTTCG CGGGAAAACT    300
GAATAAGAGG AAGTGAAATC TGAATAATTT TGTGTTACTC ATAGCGCGTA ATATTTGTCT    360
AGGGAGATCT GCTGCGCGCT CGCTCGCTCA CTGAGGCCGC CCGGGCAAAG CCCGGGCGTC    420
GGGCGACCTT TGGTCGCCCG GCCTCAGTGA GCGAGCGAGC GCGCAGAGAG GGAGTGGCCA    480
ACTCCATCAC TAGGGGTTCC TTGTAGTTAA TGATTAACCC GCCATGCTAC TTATCTACAA    540
TTCGAGCTTG CATGCCTGCA GGTCGTTACA TAACTTACGG TAAATGGCCC GCCTGGCTGA    600
CCGCCCAACG ACCCCCGCCC ATTGACGTCA ATAATGACGT ATGTTCCCAT AGTAACGCCA    660
ATAGGGACTT TCCATTGACG TCAATGGGTG GAGTATTTAC GGTAAACTGC CCACTTGGCA    720
GTACATCAAG TGTATCATAT GCCAAGTACG CCCCCTATTG ACGTCAATGA CGGTAAATGG    780
CCCGCCTGGC ATTATGCCCA GTACATGACC TTATGGGACT TTCCTACTTG GCAGTACATC    840
TACGTATTAG TCATCGCTAT TACCATGGTG ATGCGGTTTT GGCAGTACAT CAATGGGCGT    900
GGATAGCGGT TTGACTCACG GGATTTCCA AGTCTCCACC CCATTGACGT CAATGGGAGT    960
TTGTTTTGGC ACCAAAATCA ACGGGACTTT CCAAAATGTC GTAACAACTC CGCCCCATTG   1020
ACGCAAATGG GCGGTAGGCG TGTACGGTGG GAGGTCTATA TAAGCAGAGC TCGTTTAGTG   1080
AACCGTCAGA TCGCCTGGAG ACGCCATCCA CGCTGTTTTG ACCTCCATAG AAGACACCGG   1140
GACCGATCCA GCCTCCGGAC TCTAGAGGAT CCGGTACTCG AGGAACTGAA AAACCAGAAA   1200
GTTAACTGGT AAGTTTAGTC TTTTTGTCTT TTATTTCAGG TCCCGGATCC GGTGGTGGTG   1260
CAAATCAAAG AACTGCTCCT CAGTGGATGT TGCCTTTACT TCTAGGCCTG TACGAAGTG    1320
TTACTTCTGC TCTAAAAGCT GCGGAATTGT ACCCGCGGCC GCAATTCCCG GGATCGAAA    1380
GAGCCTGCTA AAGCAAAAAA GAAGTCACCA TGTCGTTTAC TTTGACCAAC AAGAACGTGA   1440
TTTTCGTTGC CGGTCTGGGA GGCATTGGTC TGGACACCAG CAAGGAGCTG CTCAAGCGCG   1500
ATCCCGTCGT TTTACAACGT CGTGACTGGG AAAACCCTGG CGTTACCCAA CTTAATCGCC   1560
TTGCAGCACA TCCCCCTTTC GCCAGCTGGC GTAATAGCGA AGAGGCCCGC ACCGATCGCC   1620
CTTCCCAACA GTTGCGCAGC CTGAATGGCG AATGGCGCTT TGCCTGGTTT CCGGCACCAG   1680
AAGCGGTGCC GGAAAGCTGG CTGGAGTGCG ATCTTCCTGA GGCCGATACT GTCGTCGTCC   1740
CCTCAAACTG GCAGATGCAC GGTTACGATG CGCCCATCTA CACCAACGTA ACCTATCCCA   1800
```

-continued

```
TTACGGTCAA TCCGCCGTTT GTTCCCACGG AGAATCCGAC GGGTTGTTAC TCGCTCACAT    1860

TTAATGTTGA TGAAAGCTGG CTACAGGAAG GCCAGACGCG AATTATTTTT GATGGCGTTA    1920

ACTCGGCGTT TCATCTGTGG TGCAACGGGC GCTGGGTCGG TTACGGCCAG GACAGTCGTT    1980

TGCCGTCTGA ATTTGACCTG AGCGCATTTT TACGCGCCGG AGAAAACCGC CTCGCGGTGA    2040

TGGTGCTGCG TTGGAGTGAC GGCAGTTATC TGGAAGATCA GGATATGTGG CGGATGAGCG    2100

GCATTTTCCG TGACGTCTCG TTGCTGCATA AACCGACTAC ACAAATCAGC GATTTCCATG    2160

TTGCCACTCG CTTTAATGAT GATTTCAGCC GCGCTGTACT GGAGGCTGAA GTTCAGATGT    2220

GCGGCGAGTT GCGTGACTAC CTACGGGTAA CAGTTTCTTT ATGGCAGGGT GAAACGCAGG    2280

TCGCCAGCGG CACCGCGCCT TTCGGCGGTG AAATTATCGA TGAGCGTGGT GGTTATGCCG    2340

ATCGCGTCAC ACTACGTCTG AACGTCGAAA ACCCGAAACT GTGGAGCGCC GAAATCCCGA    2400

ATCTCTATCG TGCGGTGGTT GAACTGCACA CCGCCGACGG CACGCTGATT GAAGCAGAAG    2460

CCTGCGATGT CGGTTTCCGC GAGGTGCGGA TTGAAAATGG TCTGCTGCTG CTGAACGGCA    2520

AGCCGTTGCT GATTCGAGGC GTTAACCGTC ACGAGCATCA TCCTCTGCAT GGTCAGGTCA    2580

TGGATGAGCA GACGATGGTG CAGGATATCC TGCTGATGAA GCAGAACAAC TTTAACGCCG    2640

TGCGCTGTTC GCATTATCCG AACCATCCGC TGTGGTACAC GCTGTGCGAC CGCTACGGCC    2700

TGTATGTGGT GGATGAAGCC AATATTGAAA CCCACGGCAT GGTGCCAATG AATCGTCTGA    2760

CCGATGATCC GCGCTGGCTA CCGGCGATGA GCGAACGCGT AACGCGAATG GTGCAGCGCG    2820

ATCGTAATCA CCCGAGTGTG ATCATCTGGT CGCTGGGGAA TGAATCAGGC CACGGCGCTA    2880

ATCACGACGC GCTGTATCGC TGGATCAAAT CTGTCGATCC TTCCCGCCCG GTGCAGTATG    2940

AAGGCGGCGG AGCCGACACC ACGGCCACCG ATATTATTTG CCCGATGTAC GCGCGCGTGG    3000

ATGAAGACCA GCCCTTCCCG GCTGTGCCGA AATGGTCCAT CAAAAAATGG CTTTCGCTAC    3060

CTGGAGAGAC GCGCCCGCTG ATCCTTTGCG AATACGCCCA CGCGATGGGT AACAGTCTTG    3120

GCGGTTTCGC TAAATACTGG CAGGCGTTTC GTCAGTATCC CCGTTTACAG GGCGGCTTCG    3180

TCTGGGACTG GGTGGATCAG TCGCTGATTA AATATGATGA AAACGGCAAC CCGTGGTCGG    3240

CTTACGGCGG TGATTTTGGC GATACGCCGA ACGATCGCCA GTTCTGTATG AACGGTCTGG    3300

TCTTTGCCGA CCGCACGCCG CATCCAGCGC TGACGGAAGC AAAACACCAG CAGCAGTTTT    3360

TCCAGTTCCG TTTATCCGGG CAAACCATCG AAGTGACCAG CGAATACCTG TTCCGTCATA    3420

GCGATAACGA GCTCCTGCAC TGGATGGTGG CGCTGGATGG TAAGCCGCTG GCAAGCGGTG    3480

AAGTGCCTCT GGATGTCGCT CCACAAGGTA AACAGTTGAT TGAACTGCCT GAACTACCGC    3540

AGCCGGAGAG CGCCGGGCAA CTCTGGCTCA CAGTACGCGT AGTGCAACCG AACGCGACCG    3600

CATGGTCAGA AGCCGGGCAC ATCAGCGCCT GGCAGCAGTG GCGTCTGGCG GAAAACCTCA    3660

GTGTGACGCT CCCCGCCGCG TCCCACGCCA TCCCGCATCT GACCACCAGC GAAATGGATT    3720

TTTGCATCGA GCTGGGTAAT AAGCGTTGGC AATTTAACCG CCAGTCAGGC TTTCTTTCAC    3780

AGATGTGGAT TGGCGATAAA AAACAACTGC TGACGCCGCT GCGCGATCAG TTCACCCGTG    3840

CACCGCTGGA TAACGACATT GGCGTAAGTG AAGCGACCCG CATTGACCCT AACGCCTGGG    3900

TCGAACGCTG GAAGGCGGCG GGCCATTACC AGGCCGAAGC AGCGTTGTTG CAGTGCACGG    3960

CAGATACACT TGCTGATGCG GTGCTGATTA CGACCGCTCA CGCGTGGCAG CATCAGGGGA    4020

AAACCTTATT TATCAGCCGG AAAACCTACC GGATTGATGG TAGTGGTCAA ATGGCGATTA    4080

CCGTTGATGT TGAAGTGGCG AGCGATACAC CGCATCCGGC GCGGATTGGC CTGAACTGCC    4140
```

-continued

| | | | | |
|---|---|---|---|---|
| AGCTGGCGCA | GGTAGCAGAG | CGGGTAAACT | GGCTCGGATT | AGGGCCGCAA GAAAACTATC | 4200 |
| CCGACCGCCT | TACTGCCGCC | TGTTTTGACC | GCTGGGATCT | GCCATTGTCA GACATGTATA | 4260 |
| CCCCGTACGT | CTTCCCGAGC | GAAAACGGTC | TGCGCTGCGG | GACGCGCGAA TTGAATTATG | 4320 |
| GCCCACACCA | GTGGCGCGGC | GACTTCCAGT | TCAACATCAG | CCGCTACAGT CAACAGCAAC | 4380 |
| TGATGGAAAC | CAGCCATCGC | CATCTGCTGC | ACGCGGAAGA | AGGCACATGG CTGAATATCG | 4440 |
| ACGGTTTCCA | TATGGGGATT | GGTGGCGACG | ACTCCTGGAG | CCCGTCAGTA TCGGCGGAAT | 4500 |
| TACAGCTGAG | CGCCGGTCGC | TACCATTACC | AGTTGGTCTG | GTGTCAAAAA TAATAATAAC | 4560 |
| CGGGCAGGCC | ATGTCTGCCC | GTATTTCGCG | TAAGGAAATC | CATTATGTAC TATTTAAAAA | 4620 |
| ACACAAACTT | TTGGATGTTC | GGTTTATTCT | TTTTCTTTTA | CTTTTTTATC ATGGGAGCCT | 4680 |
| ACTTCCCGTT | TTTCCCGATT | TGGCTACATG | ACATCAACCA | TATCAGCAAA AGTGATACGG | 4740 |
| GTATTATTTT | TGCCGCTATT | TCTCTGTTCT | CGCTATTATT | CCAACCGCTG TTTGGTCTGC | 4800 |
| TTTCTGACAA | ACTCGGCCTC | GACTCTAGGC | GGCCGCGGGG | ATCCAGACAT GATAAGATAC | 4860 |
| ATTGATGAGT | TTGGACAAAC | CACAACTAGA | ATGCAGTGAA | AAAAATGCTT TATTTGTGAA | 4920 |
| ATTTGTGATG | CTATTGCTTT | ATTTGTAACC | ATTATAAGCT | GCAATAAACA AGTTAACAAC | 4980 |
| AACAATTGCA | TTCATTTTAT | GTTTCAGGTT | CAGGGGGAGG | TGTGGGAGGT TTTTTCGGAT | 5040 |
| CCTCTAGAGT | CGAGTAGATA | AGTAGCATGG | CGGGTTAATC | ATTAACTACA AGGAACCCCT | 5100 |
| AGTGATGGAG | TTGGCCACTC | CCTCTCTGCG | CGCTCGCTCG | CTCACTGAGG CCGGGCGACC | 5160 |
| AAAGGTCGCC | CGACGCCCGG | GCTTTGCCCG | GGCGGCCTCA | GTGAGCGAGC GAGCGCGCAG | 5220 |
| CAGATCTGGA | AGGTGCTGAG | GTACGATGAG | ACCCGCACCA | GGTGCAGACC CTGCGAGTGT | 5280 |
| GGCGGTAAAC | ATATTAGGAA | CCAGCCTGTG | ATGCTGGATG | TGACCGAGGA GCTGAGGCCC | 5340 |
| GATCACTTGG | TGCTGGCCTG | CACCCGCGCT | GAGTTTGGCT | CTAGCGATGA AGATACAGAT | 5400 |
| TGAGGTACTG | AAATGTGTGG | GCGTGGCTTA | AGGGTGGGAA | AGAATATATA AGGTGGGGGT | 5460 |
| CTTATGTAGT | TTTGTATCTG | TTTTGCAGCA | GCCGCCGCCG | CCATGAGCAC CAACTCGTTT | 5520 |
| GATGGAAGCA | TTGTGAGCTC | ATATTTGACA | ACGCGCATGC | CCCCATGGGC CGGGGTGCGT | 5580 |
| CAGAATGTGA | TGGGCTCCAG | CATTGATGGT | CGCCCCGTCC | TGCCCGCAAA CTCTACTACC | 5640 |
| TTGACCTACG | AGACCGTGTC | TGGAACGCCG | TTGGAGACTG | CAGCCTCCGC CGCCGCTTCA | 5700 |
| GCCGCTGCAG | CCACCGCCCG | CGGGATTGTG | ACTGACTTTG | CTTTCCTGAG CCCGCTTGCA | 5760 |
| AGCAGTGCAG | CTTCCCGTTC | ATCCGCCCGC | GATGACAAGT | TGACGGCTCT TTTGGCACAA | 5820 |
| TTGGATTCTT | TGACCCGGGA | ACTTAATGTC | GTTTCTCAGC | AGCTGTTGGA TCTGCGCCAG | 5880 |
| CAGGTTTCTG | CCCTGAAGGC | TTCCTCCCCT | CCCAATGCGG | TTTAAAACAT AAATAAAAAA | 5940 |
| CCAGACTCTG | TTTGGATTTG | GATCAAGCAA | GTGTCTTGCT | GTCTTTATTT AGGGGTTTTG | 6000 |
| CGCGCGCGGT | AGGCCCGGGA | CCAGCGGTCT | CGGTCGTTGA | GGGTCCTGTG TATTTTTTCC | 6060 |
| AGGACGTGGT | AAAGGTGACT | CTGGATGTTC | AGATACATGG | GCATAAGCCC GTCTCTGGGG | 6120 |
| TGGAGGTAGC | ACCACTGCAG | AGCTTCATGC | TGCGGGGTGG | TGTTGTAGAT GATCCAGTCG | 6180 |
| TAGCAGGAGC | GCTGGGCGTG | GTGCCTAAAA | ATGTCTTTCA | GTAGCAAGCT GATTGCCAGG | 6240 |
| GGCAGGCCCT | TGGTGTAAGT | GTTTACAAAG | CGGTTAAGCT | GGGATGGGTG CATACGTGGG | 6300 |
| GATATGAGAT | GCATCTTGGA | CTGTATTTTT | AGGTTGGCTA | TGTTCCCAGC CATATCCCTC | 6360 |
| CGGGGATTCA | TGTTGTGCAG | AACCACCAGC | ACAGTGTATC | CGGTGCACTT GGGAAATTTG | 6420 |
| TCATGTAGCT | TAGAAGGAAA | TGCGTGGAAG | AACTTGGAGA | CGCCCTTGTG ACCTCCAAGA | 6480 |
| TTTTCCATGC | ATTCGTCCAT | AATGATGGCA | ATGGGCCCAC | GGGCGGCGGC CTGGGCGAAG | 6540 |

```
ATATTTCTGG GATCACTAAC GTCATAGTTG TGTTCCAGGA TGAGATCGTC ATAGGCCATT    6600

TTTACAAAGC GCGGGCGGAG GGTGCCAGAC TGCGGTATAA TGGTTCCATC CGGCCCAGGG    6660

GCGTAGTTAC CCTCACAGAT TTGCATTTCC CACGCTTTGA GTTCAGATGG GGGGATCATG    6720

TCTACCTGCG GGGCGATGAA GAAAACGGTT TCCGGGGTAG GGGAGATCAG CTGGGAAGAA    6780

AGCAGGTTCC TGAGCAGCTG CGACTTACCG CAGCCGGTGG GCCCGTAAAT CACACCTATT    6840

ACCGGGTGCA ACTGGTAGTT AAGAGAGCTG CAGCTGCCGT CATCCCTGAG CAGGGGGGCC    6900

ACTTCGTTAA GCATGTCCCT GACTCGCATG TTTTCCCTGA CCAAATCCGC CAGAAGGCGC    6960

TCGCCGCCCA GCGATAGCAG TTCTTGCAAG GAAGCAAAGT TTTTCAACGG TTTGAGACCG    7020

TCCGCCGTAG GCATGCTTTT GAGCGTTTGA CCAAGCAGTT CCAGGCGGTC CCACAGCTCG    7080

GTCACCTGCT CTACGGCATC TCGATCCAGC ATATCTCCTC GTTTCGCGGG TTGGGGCGGC    7140

TTTCGCTGTA CGGCAGTAGT CGGTGCTCGT CCAGACGGGC CAGGGTCATG TCTTTCCACG    7200

GGCGCAGGGT CCTCGTCAGC GTAGTCTGGG TCACGGTGAA GGGGTGCGCT CCGGGCTGCG    7260

CGCTGGCCAG GGTGCGCTTG AGGCTGGTCC TGCTGGTGCT GAAGCGCTGC CGGTCTTCGC    7320

CCTGCGCGTC GGCCAGGTAG CATTTGACCA TGGTGTCATA GTCCAGCCCC TCCGCGGCGT    7380

GGCCCTTGGC GCGCAGCTTG CCCTTGGAGG AGGCGCCGCA CGAGGGGCAG TGCAGACTTT    7440

TGAGGGCGTA GAGCTTGGGC GCGAGAAATA CCGATTCCGG GGAGTAGGCA TCCGCGCCGC    7500

AGGCCCCGCA GACGGTCTCG CATTCCACGA GCCAGGTGAG CTCTGGCCGT TCGGGGTCAA    7560

AAACCAGGTT TCCCCCATGC TTTTTGATGC GTTTCTTACC TCTGGTTTCC ATGAGCCGGT    7620

GTCCACGCTC GGTGACGAAA AGGCTGTCCG TGTCCCGTA TACAGACTTG AGAGGCCTGT    7680

CCTCGACCGA TGCCCTTGAG AGCCTTCAAC CCAGTCAGCT CCTTCCGGTG GGCGCGGGC    7740

ATGACTATCG TCGCCGCACT TATGACTGTC TTCTTTATCA TGCAACTCGT AGGACAGGTG    7800

CCGGCAGCGC TCTGGGTCAT TTTCGGCGAG GACCGCTTTC GCTGGAGCGC GACGATGATC    7860

GGCCTGTCGC TTGCGGTATT CGGAATCTTG CACGCCCTCG CTCAAGCCTT CGTCACTGGT    7920

CCCGCCACCA AACGTTTCGG CGAGAAGCAG GCCATTATCG CCGGCATGGC GGCCGACGCG    7980

CTGGGCTACG TCTTGCTGGC GTTCGCGACG CGAGGCTGGA TGGCCTTCCC CATTATGATT    8040

CTTCTCGCTT CCGGCGGCAT CGGGATGCCC GCGTTGCAGG CCATGCTGTC CAGGCAGGTA    8100

GATGACGACC ATCAGGGACA GCTTCAAGGA TCGCTCGCGG CTCTTACCAG CCTAACTTCG    8160

ATCACTGGAC CGCTGATCGT CACGGCGATT TATGCCGCCT CGGCGAGCAC ATGGAACGGG    8220

TTGGCATGGA TTGTAGGCGC CGCCCTATAC CTTGTCTGCC TCCCCGCGTT GCGTCGCGGT    8280

GCATGGAGCC GGGCCACCTC GACCTGAATG GAAGCCGGCG GCACCTCGCT AACGGATTCA    8340

CCACTCCAAG AATTGGAGCC AATCAATTCT TGCGGAGAAC TGTGAATGCG CAAACCAACC    8400

CTTGGCAGAA CATATCCATC GCGTCCGCCA TCTCCAGCAG CCGCACGCGG CGCATCTCGG    8460

GCAGCGTTGG GTCCTGGCCA CGGGTGCGCA TGATCGTGCT CCTGTCGTTG AGGACCCGGC    8520

TAGGCTGGCG GGGTTGCCTT ACTGGTTAGC AGAATGAATC ACCGATACGC GAGCGAACGT    8580

GAAGCGACTG CTGCTGCAAA ACGTCTGCGA CCTGAGCAAC AACATGAATG GTCTTCGGTT    8640

TCCGTGTTTC GTAAAGTCTG GAAACGCGGA AGTCAGCGCC CTGCACCATT ATGTTCCGGA    8700

TCTGCATCGC AGGATGCTGC TGGCTACCCT GTGGAACACC TACATCTGTA TTAACGAAGC    8760

CTTTCTCAAT GCTCACGCTG TAGGTATCTC AGTTCGGTGT AGGTCGTTCG CTCCAAGCTG    8820

GGCTGTGTGC ACGAACCCCC CGTTCAGCCC GACCGCTGCG CCTTATCCGG TAACTATCGT    8880
```

```
CTTGAGTCCA AACCCGGTAAG ACACGACTTA TCGCCACTGG CAGCAGCCAC TGGTAACAGG      8940

ATTAGCAGAG CGAGGTATGT AGGCGGTGCT ACAGAGTTCT TGAAGTGGTG GCCTAACTAC      9000

GGCTACACTA GAAGGACAGT ATTTGGTATC TGCGCTCTGC TGAAGCCAGT TACCTTCGGA      9060

AAAAGAGTTG GTAGCTCTTG ATCCGGCAAA CAAACCACCG CTGGTAGCGG TGGTTTTTTT      9120

GTTTGCAAGC AGCAGATTAC GCGCAGAAAA AAAGGATCTC AAGAAGATCC TTTGATCTTT      9180

TCTACGGGGT CTGACGCTCA GTGGAACGAA AACTCACGTT AAGGGATTTT GGTCATGAGA      9240

TTATCAAAAA GGATCTTCAC CTAGATCCTT TTAAATTAAA AATGAAGTTT TAAATCAATC      9300

TAAAGTATAT ATGAGTAAAC TTGGTCTGAC AGTTACCAAT GCTTAATCAG TGAGGCACCT      9360

ATCTCAGCGA TCTGTCTATT TCGTTCATCC ATAGTTGCCT GACTCCCCGT CGTGTAGATA      9420

ACTACGATAC GGGAGGGCTT ACCATCTGGC CCCAGTGCTG CAATGATACC GCGAGACCCA      9480

CGCTCACCGG CTCCAGATTT ATCAGCAATA AACCAGCCAG CCGGAAGGGC CGAGCGCAGA      9540

AGTGGTCCTG CAACTTTATC CGCCTCCATC CAGTCTATTA ATTGTTGCCG GGAAGCTAGA      9600

GTAAGTAGTT CGCCAGTTAA TAGTTTGCGC AACGTTGTTG CCATTGCTGC AGGCATCGTG      9660

GTGTCACGCT CGTCGTTTGG TATGGCTTCA TTCAGCTCCG GTTCCCAACG ATCAAGGCGA      9720

GTTACATGAT CCCCCATGTT GTGCAAAAAA GCGGTTAGCT CCTTCGGTCC TCCGATCGTT      9780

GTCAGAAGTA AGTTGGCCGC AGTGTTATCA CTCATGGTTA TGGCAGCACT GCATAATTCT      9840

CTTACTGTCA TGCCATCCGT AAGATGCTTT TCTGTGACTG GTGAGTACTC AACCAAGTCA      9900

TTCTGAGAAT AGTGTATGCG GCGACCGAGT TGCTCTTGCC CGGCGTCAAC ACGGGATAAT      9960

ACCGCGCCAC ATAGCAGAAC TTTAAAAGTG CTCATCATTG GAAAACGTTC TTCGGGGCGA      10020

AAACTCTCAA GGATCTTACC GCTGTTGAGA TCCAGTTCGA TGTAACCCAC TCGTGCACCC      10080

AACTGATCTT CAGCATCTTT TACTTTCACC AGCGTTTCTG GGTGAGCAAA AACAGGAAGG      10140

CAAAATGCCG CAAAAAAGGG AATAAGGGCG ACACGGAAAT GTTGAATACT CATACTCTTC      10200

CTTTTTCAAT ATTATTGAAG CATTTATCAG GGTTATTGTC TCATGAGCGG ATACATATTT      10260

GAATGTATTT AGAAAAATAA ACAAATAGGG GTTCCGCGCA CATTTCCCCG AAAAGTGCCA      10320

CCTGACGTCT AAGAAACCAT TATTATCATG ACATTAACCT ATAAAAATAG GCGTATCACG      10380

AGGCCCTTTC GTCTTCAA                                                    10398

(2) INFORMATION FOR SEQ ID NO: 2:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 2:

GGCCTCTAGA TGGAGGGGTG GAGTCGTGAC                                       30

(2) INFORMATION FOR SEQ ID NO: 3:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 3:
```

```
GGCCGGATCC AACGCGCAGC CGCCATGCCG                                    30

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 4:

GGCCGGATCC CAAACCTCCC GCTTCAAAAT                                    30

(2) INFORMATION FOR SEQ ID NO: 5:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: other nucleic acid (xi) SEQUENCE DESCRIPTION: SEQ ID NO: 5:

GGCCGAGCTC AGGCTGGGTT TTGGGGAGCA                                    30
```

METHODS USING CRE-LOX FOR PRODUCTION OF RECOMBINANT ADENO-ASSOCIATED VIRUSES

CROSS-REFERENCE TO RELATED APPLICATIONS

This application is a continuation of U.S. patent application Ser. No. 09/242,743, filed Feb. 22, 1999, which will issue as U.S. Pat. No. 6,274,354, on Aug. 14, 2001, which is a 371 of PCT/US97/15691, filed Sep. 4, 1997, which claims the benefit of U.S. Provisional Application No. 60/025,323, filed Sep. 6, 1996, abandoned.

BACKGROUND OF THE INVENTION

This invention relates generally to production methods for recombinant viruses, and more specifically, to methods of producing recombinant adeno-associated viruses.

Adeno-associated virus (AAV) is a replication-deficient parvovirus, the genome of which is about 4.6 kb in length, including 145 nucleotide inverted terminal repeats (ITRs). Two open reading frames encode a series of rep and cap polypeptides. Rep polypeptides (rep78, rep68, rep62 and rep40) are involved in replication, rescue and integration of the AAV genome. The cap proteins (VP1, VP2 and VP3) form the virion capsid. Flanking the rep and cap open reading frames at the 5' and 3' ends are 145 bp inverted terminal repeats (ITRs), the first 125 bp of which are capable of forming Y- or T-shaped duplex structures. Of importance for the development of AAV vectors, the entire rep and cap domains can be excised and replaced with a therapeutic or reporter transgene [B. J. Carter, in "Handbook of Parvoviruses", ed., P. Tijsser, CRC Press, pp.155–168 (1990)]. It has been shown that the ITRs represent the minimal sequence required for replication, rescue, packaging, and integration of the AAV genome.

When this nonpathogenic human virus infects a human cell, the viral genome integrates into chromosome 19 resulting in latent infection of the cell. Production of infectious virus and replication of the virus does not occur unless the cell is coinfected with a lytic helper virus, such as adenovirus or herpesvirus. Upon infection with a helper virus, the AAV provirus is rescued and amplified, and both AAV and helper virus are produced. The infecting parental ssDNA is expanded to duplex replicating form (RF) DNAs in a rep dependent manner. The rescued AAV genomes are packaged into preformed protein capsids (icosahedral symmetry approximately 20 nm in diameter) and released as infectious virions that have packaged either + or –ss DNA genomes following cell lysis.

AAV possesses unique features that make it attractive as a vector for delivering foreign DNA to cells. Various groups have studied the potential use of AAV in the treatment of disease states. Progress towards establishing AAV as a transducing vector for gene therapy has been slow for a variety of reasons. While the ability of AAV to integrate in quiescent cells is important in terms of long term expression of a potential transducing gene, the tendency of the integrated provirus to preferentially target only specific sites in chromosome 19 reduces its usefulness.

However, an obstacle to the use of AAV for delivery of DNA is lack of highly efficient schemes for encapsidation of recombinant genomes and production of infectious virions. See, R. Kotin, Hum. Gene Ther., 5:793–801 (1994)]. One such method involves transfecting the rAAV genome into host cells followed by co-infection with wild-type AAV and adenovirus. However, this method leads to unacceptably high levels of wild-type AAV. Incubation of cells with rAAV in the absence of contaminating wild-type AAV or helper adenovirus is associated with little recombinant gene expression. In the absence of rep, integration is inefficient and not directed to chromosome 19.

A widely recognized means for manufacturing transducing AAV virions entails co-transfection with two different, yet complementing plasmids. One of these contains the therapeutic or reporter transgene sandwiched between the two cis acting AAV ITRs. The AAV components that are needed for rescue and subsequent packaging of progeny recombinant genomes are provided in trans by a second plasmid encoding the viral open reading frames for rep and cap proteins. Overexpression of Rep proteins have some inhibitory effects on adenovirus and cell growth [J. Li et al, J. Virol., 71:5236–5243 (1997)]. This toxicity has been the major source of difficulty in providing these genes in trans for the construction of a usefull rAAV gene therapy vector.

There remains a need in the art for the methods permitting the efficient production of AAV and recombinant AAV viruses for use as vectors for somatic gene therapy.

SUMMARY OF THE INVENTION

The present invention provides methods which permit efficient production of rAAV, which overcome the difficulties faced by the prior art. This method is particularly desirable for production of recombinant AAV vectors useful in gene therapy. The method involves providing a host cell with (a) a cre transgene, which permits splicing out of the rep and cap gene inhibitory sequences that when removed lead to activation of rep and cap;

(b) the AAV rep and cap genes, 5' to these genes is a spacer which is flanked by lox sites;

(c) a minigene comprising a therapeutic transgene flanked by AAV inverse terminal repeats (ITRs); and (d) adenovirus or herpesvirus helper functions.

Thus, in one aspect, the invention provides a method for producing a rAAV which comprises introducing into a host cell a first vector containing the cre transgene under regulatory control of sequences which express the gene product thereof in vitro, a second vector containing a spacer flanked by lox sites, which is 5' to the rep and cap genes, and a third vector containing a therapeutic transgene flanked by AAV ITRs. These vectors may be plasmids or recombinant viruses. One of the vectors can be a recombinant adenovirus or herpesvirus, which can provide to the host cell the essential viral helper functions to produce a rAAV particle. However, if all the vectors are plasmids, the cell must also be infected with the desired helper virus. The cell is then cultured under conditions permitting production of the cre recombinase. The recombinase causes deletion of the spacer flanked by lox sites upstream of the rep/cap genes. Removal of the spacer allows the rep and cap genes to be expressed, which in turn allows packaging of the therapeutic transgene flanked by AAV ITRs. The RAAV is harvested thereafter.

In another aspect, the invention provides a method wherein a host cell expressing cre recombinase is co-transfected with a vector carrying a spacer flanked by lox sites 5' to the rep and cap genes, and a vector containing the therapeutic minigene above. With the provision of helper functions by a means described herein, the cell is then cultured under appropriate conditions. When cultured, the cre recombinase causes deletion of the spacer thus activating expression of rep/cap, resulting in the rAAV as described above.

In yet another aspect, the present invention provides rAAV vectors produced by the methods of the invention.

Other aspects and advantages of the present invention are described further in the following detailed description of the preferred embodiments thereof.

DETAILED DESCRIPTION OF THE INVENTION

Figure 1:
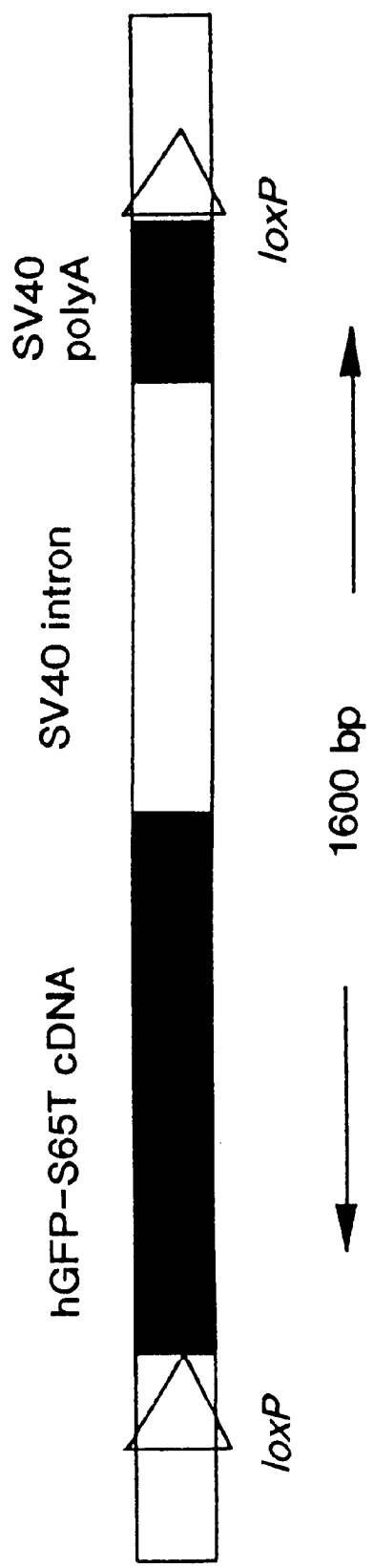
FIG. 1 is a schematic illustration of a 1600 bp DNA fragment containing green fluorescent protein (GFP) cDNA, an intron and a polyadenylation (pA or polyA) signal useful as a spacer in a vector of the invention.

The invention provides a method for rAAV production using the cre-lox system, which overcomes the difficulties previously experienced in providing efficient production systems for recombinant AAV. The method of this invention produces rAAV carrying therapeutic transgenes, which are particularly usefuil in gene therapy applications.

In summary, the method involves culturing a selected host cell which contains (a) a cre transgene (b) the AAV rep and cap genes, 5' to these genes is a spacer flanked by lox sites;

(c) a minigene comprising a therapeutic transgene flanked by AAV ITRs; and (d) adenovirus or herpesvirus helper functions.

The use of the term "vector" throughout this specification refers to either plasmid or viral vectors, which permit the desired components to be transferred to the host cell via transfection or infection. By the term "host cell" is meant any mammalian cell which is capable of functioning as an adenovirus packaging cell, i.e., expresses any adenovirus proteins essential to the production of AAV, such as HEK 293 cells and other packaging cells. By the term "minigene" is meant the sequences providing a therapeutic transgene in operative association with regulatory sequences directing expression thereof in the host cell and flanked by AAV ITRs. The term "transgene" means a heterologous gene inserted into a vector.

Desirably, components (a), (b) and (c) may be carried on separate plasmid sequences, or carried as a transgene in a recombinant virus. Alternatively, the cre protein may be expressed by the selected host cell, therefor not requiring transfection by a vector. For each of these components, recombinant adenoviruses are currently preferred. However, using the information provided herein and known techniques, one of skill in the art could readily construct a different recombinant virus (i.e., non-adenovirus) or a plasmid vector which is capable of driving expression of the selected component in the host cell. For example, although less preferred because of their inability to infect non-dividing cells, vectors carrying the required elements of this system, e.g., the cre recombinase, may be readily constructed using e.g., retroviruses or baculoviruses. Therefore, this invention is not limited by the virus or plasmid selected for purposes of introducing the cre recombinase, rep/cap, or minigene into the host cell.

Desirably, however, at least one of the vectors is a recombinant virus which also supplies the helper functions (d) to the cell. Alternatively, the helper functions may be supplied by co-infecting the cell with a helper virus, i.e., adenovirus or herpesvirus, in a conventional manner. The resulting rAAV containing the minigene may be isolated therefrom.

A. The Cre Transgene

The cre protein is a recombinase isolated from bacteriophage P1 which recognizes a specific sequence of 34 bp (loxP). Recombination between two loxP sites (catalyzed by the cre protein) causes, in certain cases, the loss of sequences flanked by these sites [for a review see N. Kilby et al, *Trends Genet.*, 9:413–421 (1993)]. The sequences of cre are provided in N. Sternberg et al, *J. Mol. Biol.*, 187:197–212 (1986) and may alternatively be obtained from other commercial and academic sources. The expression of the cre protein in the cell is essential to the method of this invention.

Without wishing to be bound by theory, the inventors believe that the expression of cre recombinase in the host cell permits the deletion of the "spacer" DNA sequence residing between the promoter and rep/cap genes in the second vector. This deletion of rep and cap gene inhibitory sequences, allows expression and activation of the rep and cap proteins and resulting in the replication and packaging of the AAV genome.

The cre protein may be provided in two alternative ways. The gene encoding the protein may be a separate component transfected into the desired host cell. Alternatively, the host cell selected for expression of the rAAV may express the cre protein constitutively or under an inducible promoter.

B. Triple Infection/Transfection Method

In one embodiment of the present invention, the method employs three vectors, i.e., recombinant viruses or plasmids, to infect/transfect a selected host cell for production of a rAAV. A first vector comprises the cre transgene operatively linked to expression control sequences. A second vector comprises the AAV rep and cap genes downstream of a spacer sequence which is flanked by lox sites and which itself is downstream of expression control sequences. A third vector comprises the therapeutic minigene, i.e., a transgene flanked by AAV ITRs and regulatory sequences. Suitable techniques for introducing these vectors into the host cell are discussed below and are known to those of skill in the art. When all vectors are present in a cell and the cell is provided with helper functions, the rAAV is efficiently produced.

1. First Vector

As stated above, in a preferred embodiment, a first vector is a recombinant replication-defective adenovirus containing the cre transgene operatively linked to expression control sequences in the site of adenovirus E1 deletion, e.g., Ad.CMV.NLS-CRE. See FIG. 5. Preferably, as in the examples below, the cre gene is operably linked to a suitable nuclear localization signal (NLS). A suitable NLS is a short sequence, i.e., in the range of about 21 bp, and may be readily synthesized using conventional techniques, or engineered onto the vector by including the NLS sequences in a PCR primer. As described in detail in Example 1 below, the cre gene and a nuclear localization signal (NLS) are obtained from a previously described plasmid.

Desirably, the cre gene is under the control of a cytomegalovirus (CMV) immediate early promoter/enhancer [see, e.g., Boshart et al, *Cell,* 41:521–530 (1985)]. However, other suitable promoters may be readily selected by one of skill in the art. Useful promoters may be constitutive promoters or regulated (inducible) promoters, which will enable control of the amount of the cre gene product to be expressed. For example, another suitable promoter includes, without limitation, the Rous sarcoma virus LTR promoter/enhancer. Still other promoter/enhancer sequences may be selected by one of skill in the art.

In addition, the recombinant virus also includes conventional regulatory elements necessary to drive expression of the cre recombinase in a cell transfected with the vector. Such regulatory elements are known to those of skill in the art, including without limitation, polyA sequences, origins of replication, etc.

2. Second Vector

Another, "second", vector useful in this embodiment of the method is described in Example 2 as Ad.sp.Rep/Cap. It contains the AAV rep and cap genes downstream of a spacer sequence which is flanked by lox sites and which itself is downstream of expression control sequences.

The AAV rep and cap sequences are obtained by conventional means. Preferably, the promoter is the AAV P5 promoter. However, one of skill in the art may readily substitute other suitable promoters. Examples of such promoters are discussed above in connection with the first vector.

The spacer is an intervening DNA sequence (STOP) between the promoter and the gene. It is flanked by loxP sites and contains multiple translational start and stop codons. The spacer is designed to permit use of a "Recombination-Activated Gene Expression (RAGE)" strategy [B. Sauer, *Methods Enzymol.,* 225:890–900 (1993)]. Such a strategy controls the expression of a given gene (in this case, rep/cap). The spacer must be excised by expression of the cre protein of the first vector and its interaction with the lox sequences to express rep/cap.

Figure 2:
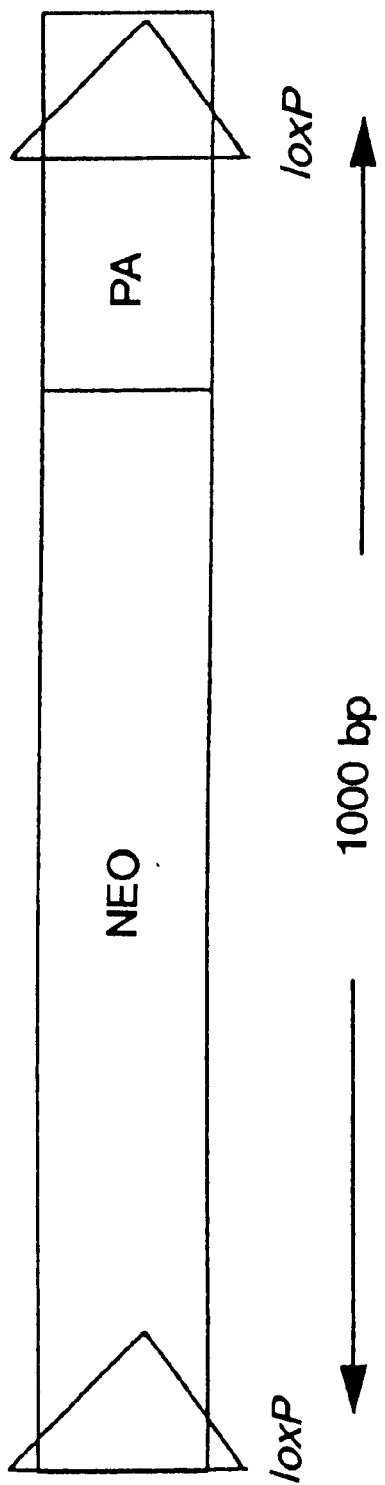
FIG. 2 is a schematic illustration of a 1000 bp DNA fragment containing the gene encoding neomycin resistance (neo$^R$) and a polyA usefril as a spacer.

Currently, there are two particularly preferred spacers. These spacers include a 1600 bp DNA fragment containing the GFP cDNA, an intron and a polyadenylation signal (FIG. 1) which was derived from a commercial plasmid (Clontech) as described below. A second preferred spacer is a 1300 bp fragment containing translational start and stop sequences obtained as a 1.3 kbp ScaI-SmaI fragment of pBS64 as described [M. Anton and F. Graham, *J. Virol.,* 69:4600–4606 (1995)]. Another desirable spacer is a 1000 bp fragment containing the neomycin resistance coding sequence and a polyadenylation signal [Y. Kanegae et al, *Nucl. Acids Res.,* 23:3816–3821 (1995)] (see, FIG. 2).

Using the information provided herein, one of skill in the art may select and design other suitable spacers, taking into consideration such factors as length, the presence of at least one set of translational start and stop signals, and optionally, the presence of polyadenylation sites. These spacers may contain genes, which typically incorporate the latter two elements (i.e., the start/stop and polyA sites). Desirably, to reduce the possibility of recombination, the spacer is less than 2 kbp in length. However, the invention is not so limited.

As stated above, the spacer is flanked by loxP sites, which are recognized by the cre protein and participate in the deletion of the spacer. The sequences of loxP are publicly available from a variety of sources [R. H. Hoess and K. Abremski, *Proc. Natl. Acad. Sci.,* 81: 1026–1029 (1984)]. Upon selection of a suitable spacer and making use of known techniques, one can readily engineer loxP sites onto the ends of the spacer sequence for use in the method of the invention.

In addition, the recombinant virus which carries the rep/cap genes and the spacer, also includes conventional regulatory elements necessary to drive expression of rep and cap in a cell transfected with the recombinant virus, following excision of the loxP-flanked spacer by the cre recombinase. Such regulatory elements are known to those of skill in the art.

3. Third Vector

The third vector contains a minigene, which is defined as a sequence which comprises a suitable transgene, a promoter, and other regulatory elements necessary for expression of the transgene, all flanked by AAV ITRs. In the examples below, where the third vector carries the LacZ gene, the presence of rAAV is detected by assays for beta-galactosidase activity. However, desirably, the third vector carries a therapeutic gene which can be delivered to an animal via the rAAV produced by this method.

The AAV sequences employed are preferably the cis-acting 5' and 3' inverted terminal repeat (ITR) sequences [See, e.g., B. J. Carter, in "Handbook of Parvoviruses", ed., P. Tijsser, CRC Press, pp.155–168 (1990)]. The ITR sequences are about 143 bp in length. Preferably, substantially the entire sequences encoding the ITRs are used in the vectors, although some degree of minor modification of these sequences is expected to be permissible for this use. The ability to modify these ITR sequences is within the skill of the art. [See, e.g., texts such as Sambrook et al, "Molecular Cloning. A Laboratory Manual.", 2d edit., Cold Spring Harbor Laboratory, New York (1989); Carter et al, cited above; and K. Fisher et al., *J. Virol.,* 70:520–532 (1996)].

The AAV ITR sequences may be obtained from any known AAV, including presently identified human AAV types. Similarly, AAVs known to infect other animals may also be employed in the vector constructs of this invention. The selection of the AAV is not anticipated to limit the following invention. A variety of AAV strains, types 1–4, are available from the American Type Culture Collection or available by request from a variety of commercial and institutional sources. In the following exemplary embodiment an AAV-2 is used for convenience.

The 5' and 3' AAV ITR sequences flank the selected transgene sequence and associated regulatory elements. The transgene sequence of the vector is a nucleic acid sequence heterologous to the AAV sequence, which encodes a polypeptide or protein of interest. The composition of the transgene sequence will depend upon the use to which the resulting vector will be put. For example, one type of transgene sequence includes a reporter sequence, which upon expression produces a detectable signal. Such reporter sequences include without limitation an *E. coli* beta-galactosidase (LacZ) cDNA, an alkaline phosphatase gene and a green fluorescent protein gene. These sequences, when associated with regulatory elements which drive their expression, provide signals detectable by conventional means, e.g., ultraviolet wavelength absorbance, visible color change, etc.

A more preferred type of transgene sequence is a therapeutic gene which expresses a desired gene product in a host cell. These therapeutic nucleic acid sequences typically encode products for administration and expression in a patient in vivo or ex vivo to replace or correct an inherited or non-inherited genetic defect or treat an epigenetic disorder or disease. The selection of the transgene sequence is not a limitation of this invention.

In addition to the major elements identified above, the minigene also includes conventional regulatory elements necessary to drive expression of the transgene in a cell transfected with this vector. Thus, the minigene comprises a selected promoter which is linked to the transgene and located within the transgene between the AAV ITR sequences.

Selection of the promoter used to drive expression of the transgene is a routine matter and is not a limitation of the vector. Useful promoters include those which are discussed above in connection with the first vector component.

The minigene also desirably contains heterologous nucleic acid sequences including sequences providing signals required for efficient polyadenylation of the transcript and introns with functional splice donor and acceptor sites. A common poly-A sequence which is employed in the exemplary vectors of this invention is that derived from the papovavirus SV-40. The poly-A sequence generally is inserted following the transgene sequences and before the 3' AAV ITR sequence. A common intron sequence is also derived from SV-40, and is referred to as the SV-40 T intron sequence. A minigene of the present invention may also contain such an intron, desirably located between the promoter/enhancer sequence and the transgene. Selection of these and other common vector elements are conventional and many such sequences are available [see, e.g., Sambrook et al, and references cited therein].

The rAAV vector containing the minigene may be carried on a plasmid backbone and used to transfect a selected host cell or may be flanked by viral sequences (e.g., adenoviral sequences) which permit it to infect the selected host cell. Suitable Ad/AAV recombinant viruses may be produced in accordance with known techniques. See, e.g., International patent applications WO96/13598, published May 9, 1996; WO95/23867 published Sep. 8, 1995, and WO95/06743 published Mar. 9, 1995, which are incorporated by reference herein.

C. Host Cell/Double Infection or Transfection System

In another embodiment of the method of this invention, a packaging cell line is constructed which expresses the cre recombinase. According to this aspect of the method, this cell line expressing the cre recombinase can be substituted for the vector or plasmid bearing the cre gene, as described above. Thus, only the second and third vectors described above are subsequently introduced into the cell.

Figure 3:
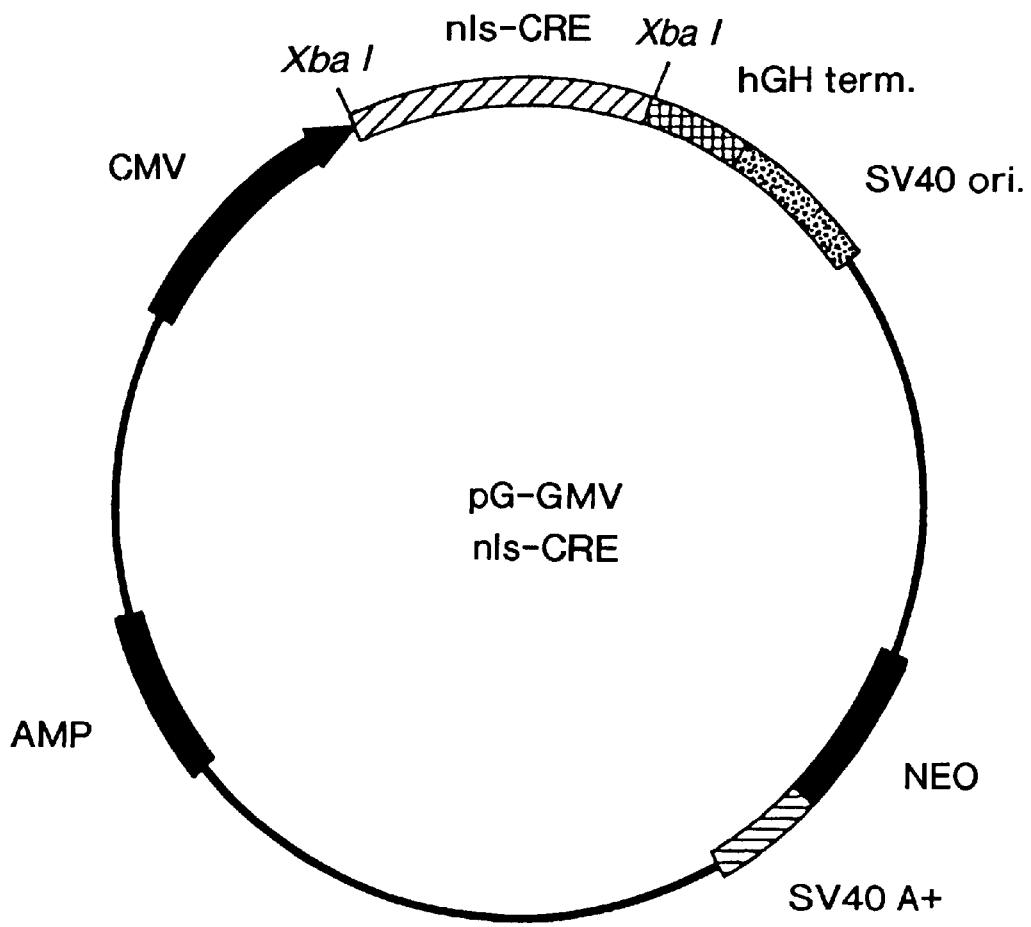
FIG. 3 illustrates a plasmid pG.CMV.nls.CRE, usefil for transfection of human embryonic kidney 293 cells in the method of the invention.

An exemplary suitable cre expressing cell line has been generated using the vector illustrated in FIG. 3. Generation of this cell line is described in detail in Example 4 below. However, the present invention is not limited to these constructs. Given the information provided herein, one of skill in the art can readily generate another plasmid containing a suitable selectable marker (e.g., $neo^R$). Such a plasmid may then be used for the generation of a cre recombinase-expressing cell line according to the invention.

Having obtained such a cre-expressing cell line, this cell line can be infected (or transfected) with the vector containing the rep/cap genes and the vector containing the minigene described above.

D. Production of Vectors and rAAV

Assembly of the selected DNA sequences contained within each of the vectors described above utilize conventional techniques. Such techniques include cDNA cloning such as those described in texts [Sambrook et al, cited above], use of overlapping oligonucleotide sequences of the adenovirus, AAV genome combined with polymerase chain reaction, and any other suitable methods which provide the desired nucleotide sequence.

Whether using the three vector system, or the cre-expressing host cell and two vectors, introduction of the vectors into the host cell is accomplished using known techniques. Where appropriate, standard transfection and co-transfection techniques are employed, e.g., $CaPO_4$ transfection techniques using the complementation human embryonic kidney (HEK) 293 cell line (a human kidney cell line containing a functional adenovirus E1a gene which provides a transacting E1a protein). Other conventional methods employed in this invention include homologous recombination of the viral genomes, plaquing of viruses in agar overlay, methods of measuring signal generation, and the like.

Following infection/transfection, the host cell is then cultured under standard conditions, to enable production of the rAAV. See, e.g., F. L. Graham and L. Prevec, *Methods Mol. Biol.*, 7:109–128 (1991). Desirably, once the rAAV is identified by conventional means, it may be recovered using standard techniques and purified.

The following examples illustrate the preferred methods of the invention. These examples are illustrative only and are not intended to limit the scope of the invention.

EXAMPLE 1

Construction of Ad.CMV.NLS-CRE

Figure 5:
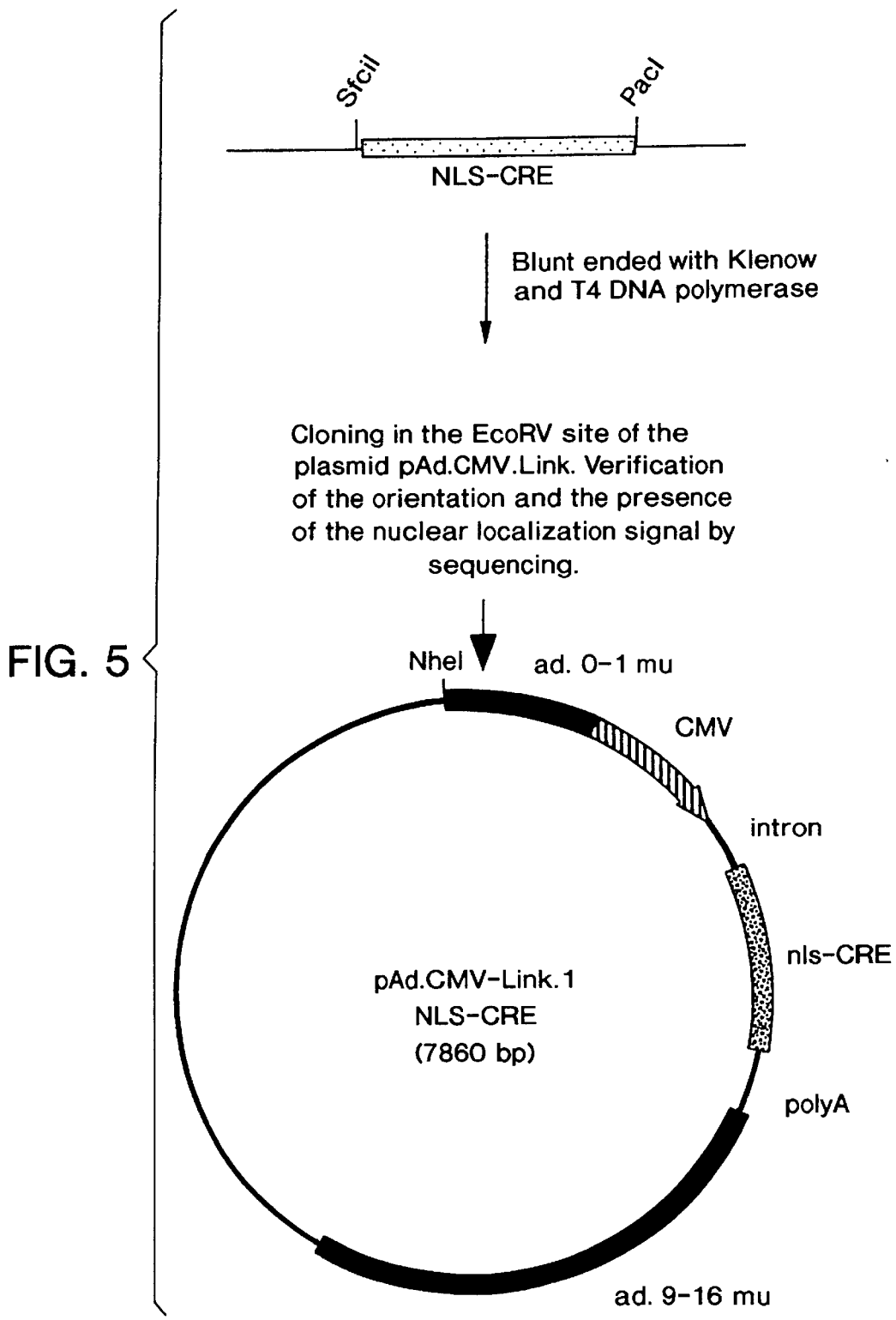
FIG. 5 illustrates the construction of the recombinant adenovirus, Ad.CMV.NLS-CRE, useful in the method of the invention.

The construction of a recombinant adenovirus containing a nuclear localization signal and the cre gene under control of a cytomegalovirus promoter is described below, with reference to FIG. 5.

The nls-Cre cDNA was isolated from the plasmid pex-CANCRE [Y. Kanegae et al, *Nucl. Acids Res.*, 23:3816–3821 (1995)] by digestion with Sfcil and Pacd and then blunt ended with Klenow and T4 DNA polymerase. The NLS-Cre fragment was then cloned into the EcoRV site of the plasmid pAd.CMV.Link (a plasmid containing the human Ad5 sequences, map units 0 to 16, which is deleted of E1a and E1b as described in X. Ye et al, *J. Biol. Chem.*, 271:3639–3646 (1996). The orientation and presence of the nuclear localization signal in the resulting plasmid pAd.CMV.NLS-CRE was verified by sequencing.

To produce the recombinant adenovirus carrying the cre transgene, the pAd.CMV.NLS-CRE recombinant vector was co-transfected with the Ad dl327 backbone into 293 cells. Ten days later, 15 plaques were picked up and 5 of them were expanded on 293 cells. Viruses were screened for their recombinase activity by assessing their ability to remove a spacer positioned between the CAG promoter (beta-actin) and the bacterial LacZ coding sequence using an adenoviral construct described in Y. Kanegae et al, *Nucl. Acids Res.*, 23:3816–3821 (1995). Two viruses tested positive for beta-galactosidase activity, indicating cre recombinase activity. As desired, these recombinant viruses may be purified by two rounds of plaque purification.

EXAMPLE 2

Construction of Ad.sp.Rep/Cap

An exemplary recombinant adenovirus containing the AAV rep and cap genes may be produced as follows.

An AAV P5 promoter was obtained from the 121 bp XbaI-BamHI fragment from plasmid psub201, which contains the entire AAV2 genome [R. J. Samulski et al, *J. Virol.*, 61:3096–3101 (1987)] by PCR using the following primer pairs:

XbaI ITR rightward: SEQ ID NO:2:
GGCCTCTAGATGGAGGGGTGGAGTCGTGAC;
BamP5 rightward: SEQ ID NO:3:
GGCCGGATCCAACGCGCAGCCGCCATGCCG;
Bam P5 leftward: SEQ ID NO:4:
GGCCGGATCCCAAACCTCCCGCTTCAAAAT;
SacI leftward: SEQ ID NO:5:
GGCCGAGCTCAGGCTGGGTTTTGGGGAGCA.

A 5' portion of the Rep/Cap gene was similarly excised via PCR from a BamI-SacI fragment (504 bp) obtained from psub201. The BamHI PCR primer creates a unique site between the rep mRNA and the first rep ATG. The P5 promoter and the Rep/Cap gene fragment were subcloned into the XbaI-SacI sites of the pSP72 vector (Promega), resulting in P5.Rep/Cap. The spacer DNA, a 1300 bp fragment flanked by loxP sites, was obtained from the plasmid pMA19 [M. Anton and F. Graham, *J. Virol.*, 69:4600–4606 (1995)] following digestion with BamHI. This spacer DNA was cloned into the unique BamHI site of the P5.Rep/Cap construct, resulting in the P5.Spacer.Rep/Cap construct.

The complete fragment containing the P5 promoter, the spacer and the rep/cap genes was obtained by subcloning the 3' portion of the Rep/Cap gene (SacI/blunt ended fragment, 3680 bp) into the SacI-EcoRV sites of the P5.Spacer.Rep/Cap plasmid. The 3' portion of the Rep/cap gene was isolated from the SSV9 plasmid (which contains a complete wild-type AAV genome) as a SacI-blunt ended fragment. This involved digesting SSV9 with XbaI, filling the XbaI site with Klenow and liberating the fragment by digesting with SacI.

The complete fragment containing the P5 promoter, the spacer and the rep/cap sequence was subcloned into the BglII site of the pAd.link vector. This was accomplished by adding a BglII linker at the 5' end of the P5.Spacer.Rep/Cap plasmid construct and using the BglII site located at the 3' end of the multiple cloning site of pSP72.

Figure 4:
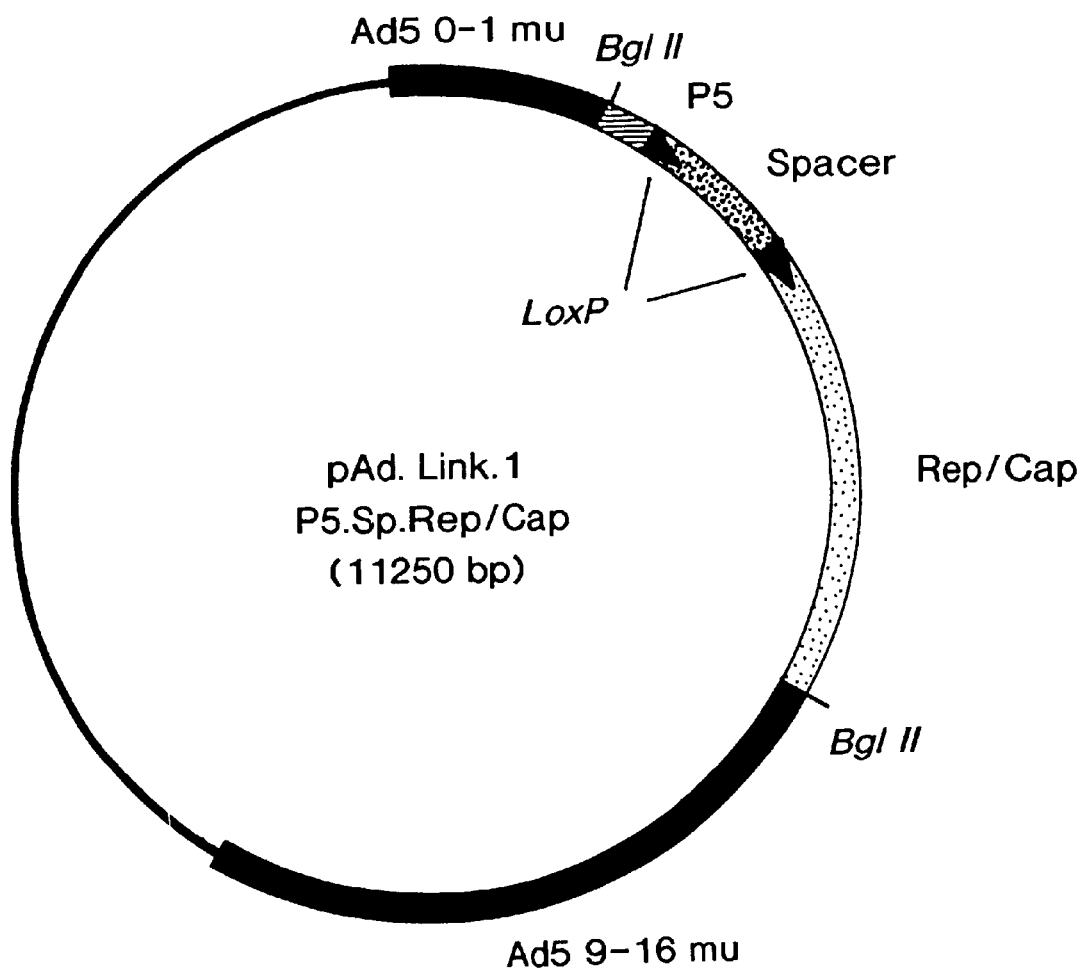
FIG. 4 illustrates a plasmid pAd.P5.Sp.Rep/Cap, useful in the method of the invention.

The resulting plasmid (11250 bp) contains Ad5 map units (mu) 0–1, the P5 promoter, the spacer sequence flanked by loxP sites, rep/cap, and Ad5 mu 9–16. This plasmid is termed pAd.P5.spacer.Rep/Cap [FIG. 4].

To produce recombinant adenovirus capable of expressing rep and cap, pAd.P5.spacer.Rep/Cap was first used to transform a cre-expressing bacterial strain *E. coli* strain BNN132 (ATCC Accession No. 47059) in order to determine whether the spacer could be removed after recombination between the loxP sites (catalyzed by the cre recombinase). Analysis on agarose gels of the plasmid DNA isolated from several transformed colonies showed that, indeed, most of the constructs analyzed lost the spacer following transformation (data not shown).

The plasmid P5.spacer.Rep/Cap was also co-transfected with the Ad dl327 backbone in HEK 293 cells. Ten days later, 20 plaques were picked up and expanded. The structure of the viruses was analyzed by Southern blot using the complete AAV genome and the 1300 bp DNA spacer as probes. One plaque (P3) showed the expected band pattern after digestion with the restriction enzyme BamHI (data not shown).

Similar constructs may be made using other suitable spacers. For example, a 1600 bp spacer was derived from plasmid phGFP-S65T plasmid (Clontech) which contains the humanized GFP gene. phGFP-S65T was cut with the restriction enzymes HindIIUI and BamHI. After adding a BglII linker at the 5' end (BglII is compatible with BamHI), the 1.6 kb fragment was subdloned into the BamIH site of the flox vector [H. Gu et al, *Science*, 265:103–106 (1994)] in order to add a loxP site on each side of the fragment. The GFP DNA fragment flanked by loxP sites was subsequently cut with PvuI and SmaI and subdloned into the EcoRV site of the Bluescript II cloning vector (Stratagene). The resulting GFP spacer can be used to construct a P5.spacer.Rep/cap plasmid or adenovirus as described above.

EXAMPLE 3

Production of rAAV

The supernatant from several plaques (containing viruses) obtained from the study described in Example 2 was tested for the ability to produce AAV in a functional assay involving the adenovirus encoding the cre protein constructed as described in Example 1 above and pAV.CMVLacZ.

The plasmid AV.CMVLacZ is a rAAV cassette in which rep and cap genes are replaced with a minigene expressing β-galactosidase from a CMV promoter. The linear arrangement of AV.CMVLacZ includes:

(a) the 5' AAV ITR (bp 1–173) obtained by PCR using pAV2 [C. A. Laughlin et al, *Gene*, 23: 65–73 (1983)] as template [nucleotide numbers 365–538 of SEQ ID NO:1];

(b) a CMV immediate early enhancer/promoter [Boshart et al, *Cell*, 41:521–530 (1985); nucleotide numbers 563–1157 of SEQ ID NO: 1], (c) an SV40 intron (nucleotide numbers 1178–1179 of SEQ ID NO: 1), (d) *E. coli* beta-galactosidase cDNA (nucleotide numbers 1356–4827 of SEQ ID NO: 1), (e) an SV40 polyadenylation signal (a 237 BamHI-BclI restriction fragment containing the cleavage/poly-A signals from both the early and late transcription units; nucleotide numbers 4839–5037 of SEQ ID NO:1) and (f) 3'AAV ITR, obtained from pAV2 as a SnaBI-BglII fragment (nucleotide numbers 5053–5221 of SEQ ID NO:1).

The functional assay was performed by infecting 293 cells with the cre virus and the Rep/Cap virus (multiplicity of infection (MOI) 10) followed by a transfection 2 hours later with 5 μg pAV.CMVLacZ. Forty-eight hours later, cells were harvested and freeze-thawed. One-fifth of the supernatant (containing rAAV) was used to infect 293 cells. Twenty-four hours later an X-gal assay was performed.

Viruses from plaque #3 yielded positive for beta-galactosidase transduction in this assay. Supernatant from plaque #3 was used in a second round of purification (plaque amplification). Twenty plaques were picked up and expanded.

EXAMPLE 4

Production of Cre Expressing Cell Line

A plasmid vector, pG.CMV.nls.cre was constructed as follows for use in transfecting 293 cells. The nls-Cre cDNA was isolated from the plasmid pexCANCRE (Kanegae, cited above) as described in Example 1 above. The nls-Cre fragment was then subcloned into the XbaI sites of vector pG downstream of a CMV promoter. This plasmid vector is illustrated in FIG. 3 and contains a human growth hormone (hGH) termination sequence, an SV40 ori signal, a neomycin resistance marker, an SV40 polyadenylation site, an ampicillin marker, on a backbone of pUC19.

Figure 6A:
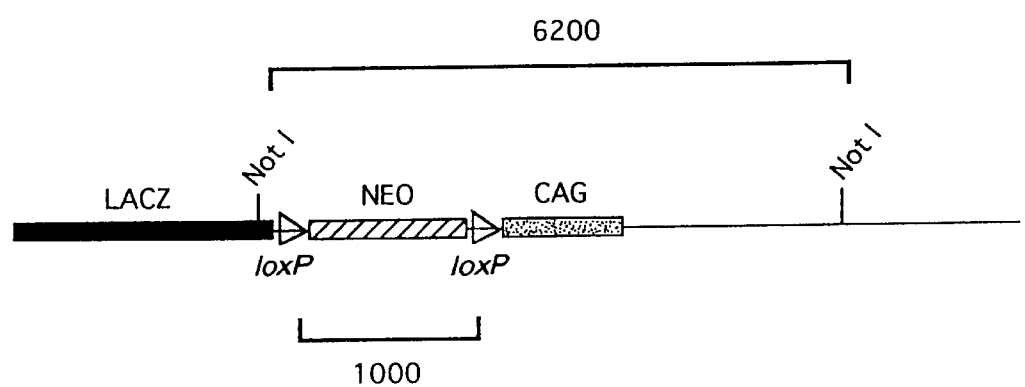
FIG. 6A illustrates the structure of the Ad.CAG.Sp.LacZ virus.
Figures 6B, 6C, 6D:
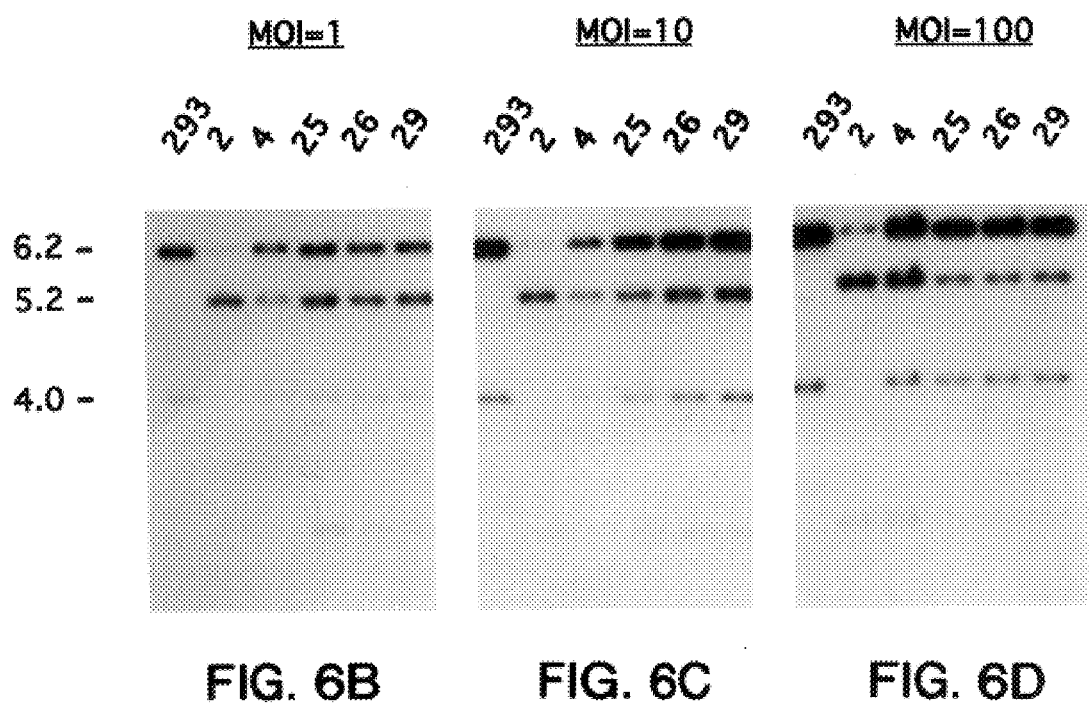
FIG. 6B provides the Southern blot analysis of genomic DNA isolated from 293 cells infected with the LacZ virus at a m.o.i. of 1 and cut with NotI. The 1000 bp $^{32}$p-NEO spacer was used as a probe. After the digestion with NotI a 6200 bp restriction fragment (without cre-mediated recombination) and/or a 5200 bp restriction fragment (with cre-mediated recombination) can be detected.
FIG. 6C provides the Southern blot analysis of genomic DNA isolated from 293 cells infected with the LacZ virus at a m.o.i. of 10 and cut with NotI. The 1000 bp $^{32}$P-NEO spacer was used as a probe. After the digestion with NotI a 6200 bp restriction fragment (without cre-mediated recombination) and/or a 5200 bp restriction fragment (with cre-mediated recombination) can be detected.
FIG. 6D provides the Southern blot analysis genomic DNA isolated from 293 cells infected with the LacZ virus at a m.o.i. of 100 and cut with NotI. The 1000 bp $^{32}$P-NEO spacer was used as a probe. After the digestion with NotI a 6200 bp restriction fragment (without cre-mediated recombination) and/or a 5200 bp restriction fragment (with cre-mediated recombination) can be detected.

This plasmid was transfected into 293 cells using conventional techniques. Cells were selected in the presence of G-418 for neomycin resistance. Cells were identified by infecting them at different MOI (1 to 100) with Ad.CAG.Sp.LacZ, an adenovirus containing the bacterial LacZ coding sequence separated from its beta-actin (CAG) promoter by a neomycin spacer DNA flanked by two loxP sites followed by the bacterial LacZ gene. Cells were selected on the basis of their ability to remove the spacer fragment inducing the expression of the LacZ gene. After X-gal staining, six cell lines were found to be positive. DNA from these infected cells was isolated and analyzed by Southern blot using the spacer DNA (NEO) as a probe. Results shown in FIG. 6A, with reference to Table 1, and FIGS. 6B–6D indicate that cell line #2 can remove the DNA spacer with much more efficacy than the other 293/cre cell lines analyzed.

TABLE 1

| NEO Probe | |
|---|---|
| Without Recombination | With Recombination |
| 6200 | 6200 |
| | 5200 |

EXAMPLE 5

Generation of the Ad.GFP Rep/Cap

As described in Example 2 for the construction of the Ad.Sp.Rep/Cap virus, the link plasmid containing the P5 promoter, the GFP spacer flanked by two loxP sites and the Rep and Cap coding sequences was co-transfected with the Ad dl327 backbone into HEK 293 cells. Ten days later, 20 plaques were picked up and expanded. During this expansion, the monolayer of HEK 293 cells were screened for the expression of GFP by microscopic analysis using a mercury lamp with a 470–490 nm band-pass excitation filter (Nikon). One of the monolayers (from plaque #13) showed a region positive for the expression of GFP. This region was further expanded and purified by two other rounds of plaque purification. The presence of the Ad.GFP.Rep/Cap virus was monitored by the expression of GFP, as described, and/or by the expression of the Rep and Cap proteins by Western blot analysis using specific monoclonal antibodies (American Research Products, Inc.). One cell lysate (from one purified plaque) containing the Ad.GFP rep/cap was used in order to infect 293 cells (adenovirus preparation with 40×150 mm dishes of HEK 293 cells). A total of 6.86×10$^{13}$ particles/ml were obtained after purification. This virus is currently being tested for the production of rAAV, as described in Example 3.

EXAMPLE 6

Construction of the Ad.TRE.CMV.GFP.Rep/Cap

Figure 7:
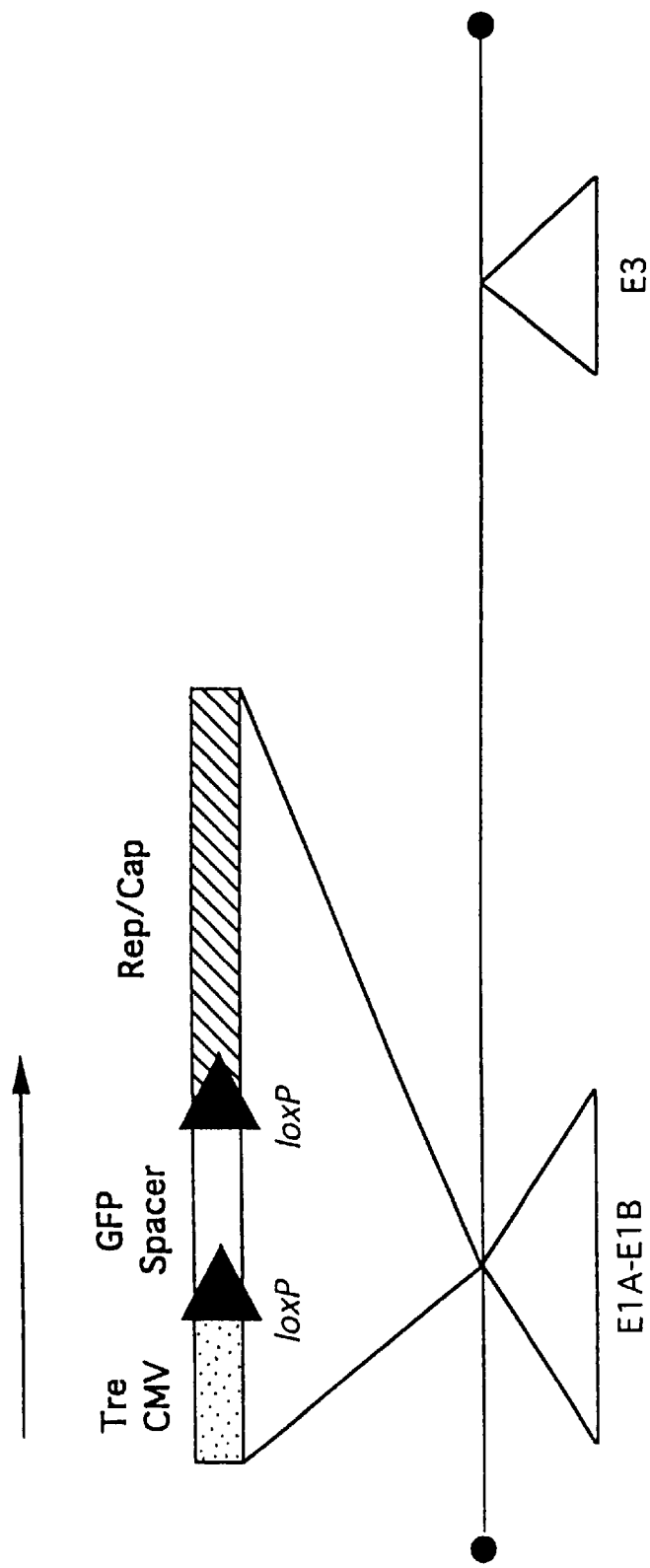
FIG. 7 illustrates the structure of the Ad.Tre.CMV.GFP.Rep/Cap virus.

FIG. 7 shows the final structure of the Ad.TRE.CMV.Rep/Cap virus. The AAV P5 promoter was replaced by the tetracycline (Tet) inducible promoter (Clontech). This promoter contains the tetracycline responsive elements (TRE) followed by the CMV minimal promoter without the CMV enhancer. This promoter is inducible in the presence of the antibiotic doxycycline (Sigma) in the 293/Tet-On cell line (Clontech) which contains a stable gene expressing the rTetR (reverse Tet repressor) fused to the GP16 transcriptional activation domain. The objective here is to construct a double inducible expression system in order to limit the expression of the cytotoxic Rep gene products. In order to fully induce the expression of the Rep and Cap genes, the virus must be in the presence of 1—the cre recombinase (in order to delete the GFP spacer as described previously) and 2—the Tet-On inducible factor doxycycline (DOX).

The link plasmid containing the construct described above was used to transfect HEK 293 cells in the presence or the absence of DOX and/or the cre recombinase (from the adenovirus expressing nls-cre). Proteins from cell homogenates were analyzed by Western blot using the Rep antibodies. Rep proteins are fully induced only in the presence of DOX and the cre recombinase.

In order to construct pAd.TRE.CMV.link. 1, the pTRE plasmid (Clontech) was cut with the restriction endonucleases Xho and EcoR1 to isolate the TRE and the minimal CMV promoter. The Xho and EcoR1 sites were filled with Klenow and the 448 bp fragment was inserted into the EcoRV site of the pAdlink. 1 plasmid. The GFP.Rep/Cap fragment was subsequently cut with ClaI and BglIII and inserted into the pAd.TRE.CMV.link. 1 cut with ClaI and BamHI.

This link recombinant plasmid was co-transfected with the Ad dl327 backbone in HEK 293 cells. Ten days later, 20 plaques were picked up and expanded. These plaques are currently being analyzed for the expression of GFP and the Rep and Cap proteins. Two adenoviruses expressing large amounts of rep proteins were identified. These viruses are currently being purified and studied.

Numerous modifications and variations of the present invention are included in the above-identified specification and are expected to be obvious to one of skill in the art. Such modifications and alterations to the processes of the present invention are believed to be encompassed in the scope of the claims appended hereto.

What is claimed is:

1. A method for production of recombinant adeno-associated virus (AAV) comprising culturing a host cell comprising:
    (a) a recombinant adenovirus comprising a cre gene under control of sequences which permit expression of cre recombinase;
    (b) a nucleic acid molecule comprising a spacer sequence flanked by lox sites, and AAV rep and cap genes, wherein the spacer sequence is upstream of the AAV genes; and
    (c) a minigene comprising a transgene flanked by AAV inverted terminal repeats (ITRs);
in the presence of helper virus functions which permit packaging of the minigene into an AAV capsid, whereby a recombinant AAV capable of expressing said transgene is produced.

2. The method according to claim 1, comprising:
    (a) introducing into a host cell
        (i) the recombinant adenovirus;
        (ii) a second vector comprising from 5' to 3', a selected promoter, a spacer sequence flanked by loxP sites, and AAV rep and AAV cap genes;
        (iii) a third vector comprising a minigene consisting essentially of, from 5' to 3', a 5' AAV ITR, a promoter, a transgene and 3' AAV ITR;
    (b) culturing the host cell under conditions which permit expression of the cre recombinase; and
    (c) recovering recombinant AAV capable of expressing the product of said transgene.

3. The method according to claim 1 wherein in the recombinant adenovirus the sequences which permit expression comprise a cytomegalovirus promoter, and the adenovirus further comprises a nuclear localization signal operably linked to the cre gene.

4. The method according to claim 1 wherein the spacer sequence is selected from the group consisting of:
    (a) a 1300 bp fragment containing translational start and stop sequences;
    (b) a 1600 bp fragment containing the green fluorescent protein (GFP) cDNA, an intron and a polyadenylation signal; and
    (c) a 1000 bp fragment containing the neomycin coding sequence and a polyadenylation signal.

5. The method according to claim 2 wherein at least one of said vectors is a recombinant adenovirus and the host cell is a 293 cell.

6. The method according to claim 2 wherein the second vector is a recombinant adenovirus and comprises an AAV P5 promoter.

* * * * *

UNITED STATES PATENT AND TRADEMARK OFFICE
CERTIFICATE OF CORRECTION

PATENT NO.    : 6,428,988 B1
DATED         : August 6, 2002
INVENTOR(S)   : J. Wilson et al.

It is certified that error appears in the above-identified patent and that said Letters Patent is hereby corrected as shown below:

Title page,
Related U.S. Application Data, replace "[63] Continuation of Application No. 09/242,743, filed as application No. PCT/US97/15691 on Sept. 4, 1997, now Pat. No. 6,274,354" with
-- [63] Continuation of Application No. 09/242,743, filed February 22, 1999, now U.S. Patent No. 6,274,354, issued on August 14, 2001, which is a 371 of PCT/US97/15691, filed September 4, 1997 --.

Column 2,
Line 57, replace "RAAV" with -- rAAV --.

Column 3,
Line 14, replace "usefril" with -- useful --.

Column 8,
Line 63, replace "Pacd" with -- PacI --.

Column 10,
Line 27, replace "subdloned into the BamIH site of" with -- subcloned into the BamHI site of --.
Line 31, replace "subdloned" with -- subcloned --.

Signed and Sealed this

Fourth Day of February, 2003

JAMES E. ROGAN
*Director of the United States Patent and Trademark Office*